(12) United States Patent
Li et al.

(10) Patent No.: US 9,778,237 B2
(45) Date of Patent: Oct. 3, 2017

(54) SYSTEMS AND METHODS FOR DETERMINING COMBUSTION PROPERTIES OF WELLHEAD GAS

(71) Applicant: Cummins, Inc., Columbus, IN (US)

(72) Inventors: Shu Li, Columbus, IN (US); Leon A. LaPointe, Columbus, IN (US); Aniket Gupta, Wuhan (CN); Matthew L. Schneider, Columbus, IN (US)

(73) Assignee: Cummins, Inc., Columbus, IN (US)

( * ) Notice: Subject to any disclaimer, the term of this patent is extended or adjusted under 35 U.S.C. 154(b) by 134 days.

(21) Appl. No.: 14/631,036

(22) Filed: Feb. 25, 2015

(65) Prior Publication Data

US 2015/0241399 A1    Aug. 27, 2015

Related U.S. Application Data

(60) Provisional application No. 61/945,621, filed on Feb. 27, 2014.

(51) Int. Cl.
| | |
|---|---|
| *G01N 33/26* | (2006.01) |
| *G01N 33/00* | (2006.01) |
| *G01N 33/22* | (2006.01) |
| *G01N 25/18* | (2006.01) |

(52) U.S. Cl.
CPC ....... *G01N 33/0036* (2013.01); *G01N 33/225* (2013.01); *G01N 25/18* (2013.01)

(58) Field of Classification Search
CPC .................................................. G01N 33/0036
See application file for complete search history.

(56) References Cited

U.S. PATENT DOCUMENTS

| | | | |
|---|---|---|---|
| 6,061,637 A | 5/2000 | Sorge et al. | |
| 8,073,636 B2 | 12/2011 | Bauer et al. | |
| 8,073,637 B2 | 12/2011 | Cline et al. | |
| 2010/0028819 A1 | 2/2010 | Knittel et al. | |

*Primary Examiner* — Laura Martin
*Assistant Examiner* — Alex Devito
(74) *Attorney, Agent, or Firm* — Foley & Lardner LLP

(57) ABSTRACT

Disclosed are methods, systems, and computer-readable mediums for determining combustion properties of wellhead gas. A methane concentration of a gas mixture is measured. A non-methane hydrocarbon concentration of the gas mixture is measured. An inert concentration of the gas mixture is calculated. A first surrogate for the non-methane hydrocarbon concentration is selected, where the first surrogate is selected as propane if the methane concentration is greater than a first threshold, and where the first surrogate is selected as pentane if the methane concentration is less than or equal to the first threshold. A methane number of the gas mixture is determined, where the methane number is based on the methane concentration, the first surrogate, and the inert concentration.

18 Claims, 6 Drawing Sheets

SYSTEMS AND METHODS FOR DETERMINING COMBUSTION PROPERTIES OF WELLHEAD GAS

CROSS-REFERENCE TO RELATED APPLICATION

This application claims the benefit of and priority to U.S. Provisional Patent Application No. 61/945,621, filed Feb. 27, 2014, entitled "SYSTEMS AND METHODS FOR DETERMINING COMBUSTION PROPERTIES OF WELLHEAD GAS," which is incorporated herein by reference in its entirety.

BACKGROUND

Typically, to provide gas quality information related to a gas mixture, the speciation of the individual hydrocarbon species of the gas mixture is performed. After speciation of the individual hydrocarbon species, various combustion properties of the gas mixture may be calculated based on the individual components of the gas mixture. The calculated combustion properties may then be utilized to adjust various operational characteristics of an engine that combusts the gas mixture. Approaches to speciation of a gas mixture include the application of Fourier Transform Infrared Spectroscopy, Gas Chromatography, and Raman scattering-based techniques.

SUMMARY

Disclosed herein are methods, systems, and computer-readable mediums for determining combustion properties of wellhead gas. One embodiment relates to a method, which comprises measuring a methane concentration of a gas mixture, measuring a non-methane hydrocarbon concentration of the gas mixture, and calculating an inert concentration of the gas mixture. The method further comprises selecting a first surrogate for the non-methane hydrocarbon concentration, where the first surrogate is selected as propane if the methane concentration is greater than a first threshold, and where the first surrogate is selected as pentane if the methane concentration is less than or equal to the first threshold. The method further comprises determining, using a computing device, a methane number of the gas mixture, wherein the methane number is based on the methane concentration, the first surrogate, and the inert concentration.

Another embodiment relates to a system, which comprises one or more computing devices. The one or more computing devices are configured to measure a methane concentration of a gas mixture, measure a non-methane hydrocarbon concentration of the gas mixture, and calculate an inert concentration of the gas mixture. The one or more computing devices are further configured to select a first surrogate for the non-methane hydrocarbon concentration, where the first surrogate is selected as propane if the methane concentration is greater than a first threshold, and where the first surrogate is selected as pentane if the methane concentration is less than or equal to the first threshold. The one or more computing devices are further configured to determine a methane number of the gas mixture, wherein the methane number is based on the methane concentration, the first surrogate, and the inert concentration.

Another embodiment relates to a method, which comprises measuring a methane concentration of a gas mixture, measuring a non-methane hydrocarbon concentration of the gas mixture, and calculating an inert concentration of the gas mixture. The method further comprises selecting a first surrogate for the non-methane hydrocarbon concentration, where the first surrogate is selected as propane if the methane concentration is greater than a first threshold, and where the first surrogate is selected as pentane if the methane concentration is less than or equal to the first threshold. The method further comprises determining, using a computing device, a methane number of the gas mixture, where the methane number is based on the methane concentration, the first surrogate, and the inert concentration. The method further comprises selecting a second surrogate for the non-methane hydrocarbon concentration, where the second surrogate is selected as a combination of ethane and propane when the methane concentration is greater than a second threshold, and where the second surrogate is selected as pentane when the methane concentration is less than or equal to the second threshold. The method further comprises determining a thermal conductivity of an approximated mixture comprising the methane concentration, the second surrogate, and the inert concentration. The method further comprises determining a difference between the approximated mixture thermal conductivity and a thermal conductivity of the gas mixture, and adjusting the second surrogate based on a third threshold and the difference between the approximated mixture thermal conductivity and the gas mixture thermal conductivity. The method further comprises determining, using the computing device, a lower heating value of the gas mixture, where the lower heating value is based on the methane concentration, the second surrogate, and the inert concentration.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several implementations in accordance with the disclosure and are, therefore, not to be considered limiting in scope, the disclosure will be described with additional specificity and detail through use of the accompanying drawings.

DETAILED DESCRIPTION

Figure 1:
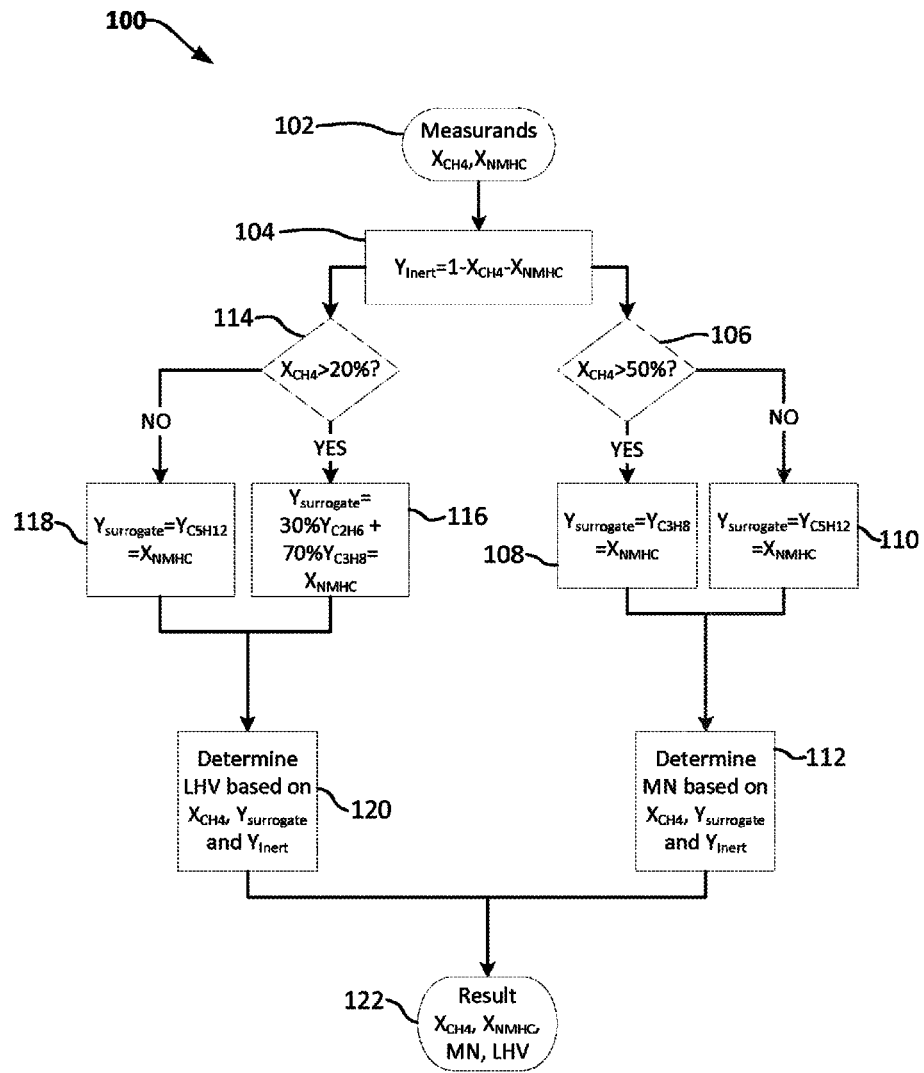
FIG. 1 shows a diagram for determining the combustion properties of a wellhead gas mixture using the input of methane and non-methane hydrocarbon contents, according to an exemplary embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that aspects of the present disclosure, as generally described herein, and illustrated in the figures, can be arranged, substituted, combined, and designed in a wide variety of different configurations, all of which are explicitly contemplated and made part of this disclosure.

Described herein are techniques for determining combustion properties of a wellhead gas mixture. In general, the combustion properties of a wellhead gas mixture (e.g., well gas that is upstream to a combustion engine) are used by an internal combustion engine (or a controller of the engine) during operation to realize various optimizations and adjustments. For example, the methane number (MN) of the gas mixture, which provides an indication of the knock tendency of the gas mixture, can be used to appropriately configure the engine (based on the methane number) to avoid knocking or to take measures to limit potential damage caused by knocking As another example, the lower heating value (LHV) of the gas mixture may also be determined and used to appropriately configure the engine. Such combustion properties may be provided to the controller of the engine (e.g., a computing system of engine, etc.) or to other systems as desired by an operator of the engine. By determining the combustion properties of the gas mixture upstream to the engine, a feed forward control system can be implemented that allows for greater fuel flexibility and configuration of the engine. Thus, the combustion properties of the gas measure can be determined prior to the time the gas mixture reaches the engine, and the engine can be configured and/or operated based on the combustion properties of the gas mixture.

Referring to FIG. 1, a diagram is shown of a process 100 for determining the combustion properties of a wellhead gas mixture, according to one embodiment. To make this determination, process 100 utilizes the input of methane and non-methane hydrocarbon contents of the gas mixture. Initially, the gas mixture is analyzed to determine the measurands 102 of methane concentration ($X_{CH4}$) and non-methane hydrocarbon concentration ($X_{NMHC}$). Various sensors and/or devices may be utilized to determine measurands 102. In one embodiment, a laser-based $CH_4$ sensor is utilized to determine the methane content of the gas mixture. In one embodiment, a system configured to measure the non-methane hydrocarbon concentration comprises one or more oxidation catalysts, a flow meter, and an oxygen sensor.

The inert content ($Y_{Inert}$) 104 of the gas mixture may then be determined, based on the methane and non-methane hydrocarbon content. In one embodiment, the inert content may be determined as the total concentration of the gas mixture minus both the methane content and the non-methane hydrocarbon content. In another embodiment, the concentration of carbon dioxide may be determined and used as the inert content (e.g., $Y_{Inert}=1-X_{CH4}-X_{NMHC}$). Any known inert gas or inert gas combination (e.g., carbon dioxide, nitrogen, etc.) may be used as the inert content.

After the measurands discussed above are determined, both the lower heating value (LHV) of the gas mixture and the methane number of the gas mixture may be calculated using a surrogate gas mixture in place of the non-methane hydrocarbon contents for the calculations. By using surrogates in this manner, the speciation of all of the hydrocarbon contents of the gas mixture can be avoided, and accurate estimations of the LHV and MN for the gas mixture may be quickly determined.

Regarding the MN determination, the methane content concentration of the gas mixture is compared to a threshold value 106, and a surrogate to be used in the determination is chosen based on the comparison. In one embodiment, the methane concentration ($X_{CH4}$) is compared to a threshold value of 50%. If the gas mixture has a methane concentration greater than the threshold (e.g., 50%), a surrogate may be selected ($Y_{surrogate}$) 108 to take the place of the non-methane hydrocarbon content ($X_{NMHC}$). In one embodiment, the surrogate is propane ($Y_{C3H8}$). However, if the methane concentration ($X_{CH4}$) is less than or equal to the threshold value of 50%, the surrogate selected ($Y^{surrogate}$) 110 to represent the non-methane hydrocarbon content ($X_{NMHC}$) may be pentane ($Y_{C5H12}$).

After the surrogate ($Y_{surrogate}$) is selected for use in the MN determination, the MN may be calculated 112 on the approximated gas mixture composition, which consists of the methane concentration ($X_{CH4}$), the surrogate ($Y_{surrogate}$) selected for the MN determination, and the inert concentration ($Y_{Inert}$). The MN may be determined according to International Organization for Standardization (ISO) standards related to calculating a methane number of a gas mixture. In one embodiment, the MN is determined according to ISO 6976 standards.

Regarding the LHV determination, the methane content concentration may also be compared to a threshold value 114. In one embodiment, the methane concentration ($X_{CH4}$) is compared to a threshold value of 20%. If the gas mixture has a methane concentration greater than the threshold (e.g., 20%), a surrogate may be selected ($Y_{surrogate}$) 116 to take the place of the non-methane hydrocarbon content ($X_{NMHC}$). In one embodiment, the surrogate is a combination of ethane ($Y_{C2H6}$) and propane ($Y_{C3H8}$). In one embodiment, the combination is 30% ethane and 70% propane, although other variations may also be used. If the methane concentration ($X_{CH4}$) is less than or equal to the threshold (e.g., 20%), the surrogate selected ($Y_{surrogate}$) 118 to represent the non-methane hydrocarbon content ($X_{NMHC}$) may be pentane ($Y_{C5H12}$).

After a surrogate ($Y_{surrogate}$) is selected for use in the LHV determination, the LHV may be calculated 120 based on the approximated gas mixture composition, which consists of the methane concentration ($X_{CH4}$), the surrogate ($Y_{surrogate}$) selected for the LHV determination, and the inert concentration ($Y_{Inert}$). The LHV may also be determined according to International Organization for Standardization (ISO) standards related to calculating a lower heating value. In one embodiment, the LHV is determined according to ISO 6976 standards. As a result 122, the calculated estimates of the MN and LHV (which were determined using the approximated gas mixtures), the methane concentration ($X_{CH4}$) the non-methane hydrocarbon concentration ($X_{NMHC}$), and any other values determined herein may be fed forward to the control systems of an engine.

In alternative embodiments, the thermal conductivity of a selected surrogate mixture may also be analyzed during the LHV and/or the MN determination. By applying the additional thermal conductivity analysis as discussed below, an increase in the accuracy of the LHV and the MN estimates may be realized.

Figure 2:
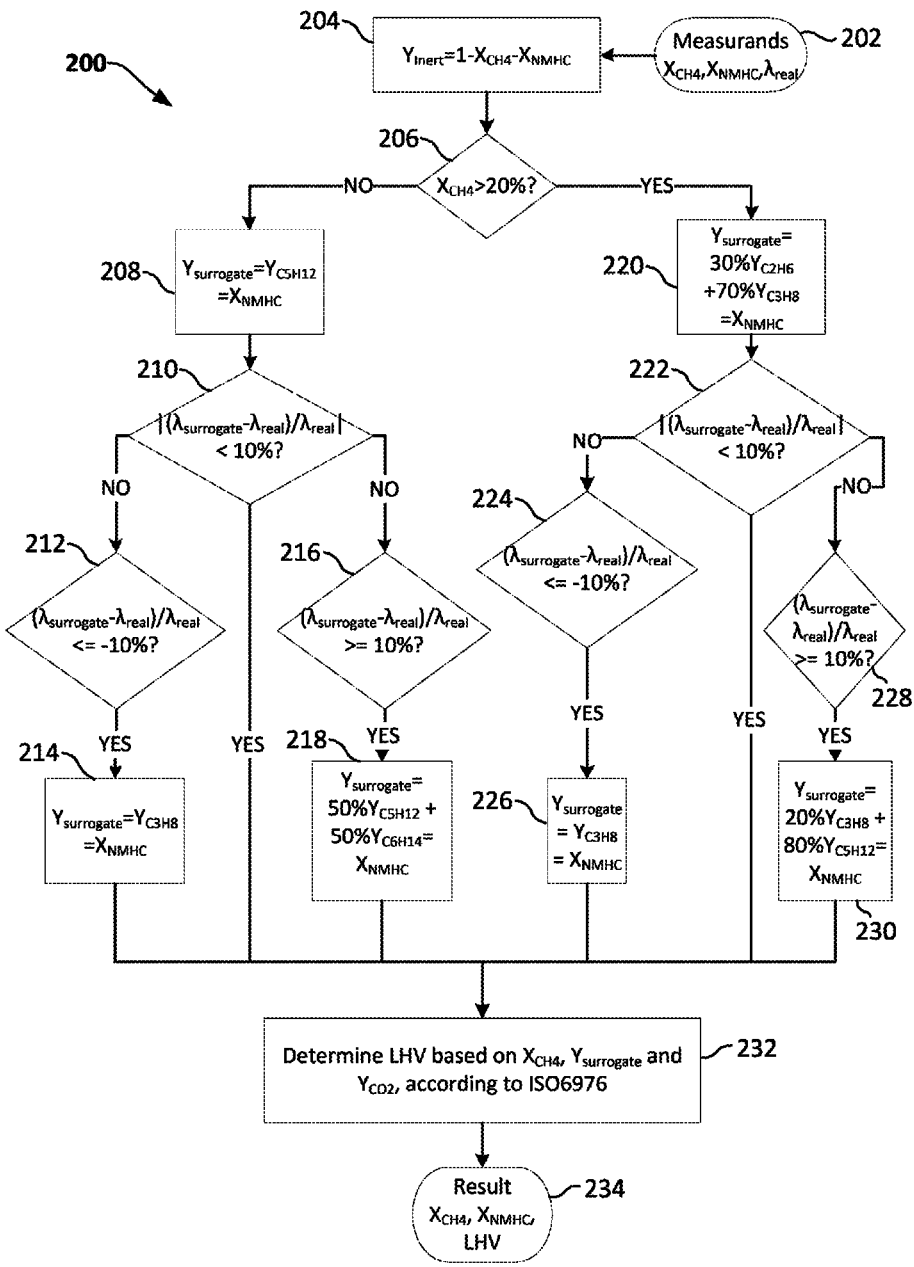
FIG. 2 shows a diagram for determining the lower heating value of a wellhead gas mixture including a thermal conductivity check, according to an exemplary embodiment.

Referring to FIG. 2, a diagram is shown of a process 200 for determining the lower heating value of a wellhead gas mixture, including a thermal conductivity check, according to one embodiment. Process 200 relates to the LHV determination as described with respect to process 100, although additional thermal conductivity analysis is performed. The thermal conductivity analysis may be based on the results of a thermal conductivity detector (TCD) that is used to determine thermal conductivity values. Initially, the gas mixture is analyzed to determine the measurands 202 of methane concentration ($X_{CH4}$) and the non-methane hydrocarbon concentration ($X_{NMHC}$). The thermal conductivity ($\lambda_{real}$) of the gas mixture is also measured using a thermal conductivity detector (TCD). The inert content ($Y_{Inert}$) 204 of the gas mixture can be determined as described above.

The methane content concentration may then be compared to a threshold value 206. In one embodiment, the methane concentration ($X_{CH4}$) is compared to a threshold value of 20%, although other thresholds may be used. If the gas mixture has a methane concentration less than or equal to the threshold (e.g., 20%), a surrogate can be selected ($Y_{surrogate}$) 208 to represent the non-methane hydrocarbon content ($X_{NMHC}$). In one embodiment, the surrogate is selected to be pentane ($Y_{C5H12}$). The measured thermal conductivity ($\lambda_{real}$) can then be compared to the calculated thermal conductivity ($\lambda_{surrogate}$) of the approximated gas mixture composed of $X_{CH4}$, $Y_{Inert}$, and $Y_{surrogate}$. The difference between the measured and calculated thermal conductivities may be used to determine whether the initial surrogate selection should be revised.

In one embodiment, if the absolute value of the percentage difference between the calculated and measured thermal conductivities is less than a threshold (e.g., 10%) 210, then the selected surrogate is not revised (e.g., $Y_{surrogate}$ remains selected as pentane ($Y_{C5H12}$)). However, if the absolute value of percentage difference is greater than or equal to the threshold (e.g., 10%) 210, then additional analysis may be performed to determine how to revise the selected surrogate. For example, if the percentage difference 212 is less than or equal to negative 10%, then the surrogate can be revised and selected as propane ($Y_{C3H8}$) 214. If the percentage difference 216 is greater than or equal to 10%, then the surrogate may be revised and selected as a combination 218 of pentane ($Y_{C5H12}$) and hexane ($Y_{C6H14}$). In one embodiment, the combination may include 50% pentane and 50% hexane. It should be understood, that the scope of the present disclosure is not limited to a 10% threshold and a 50%-50% combination of pentane and hexane, and other thresholds and combinations may be used.

Returning to the threshold comparison at 206, if the mixture has a methane concentration greater than the threshold (e.g., 20%), the surrogate can be selected ($Y_{surrogate}$) to be a combination 220 of ethane ($Y_{C2H6}$) and propane ($Y_{C3H8}$). In one embodiment, the combination is 30% ethane and 70% propane, although other combinations may be used. The measured thermal conductivity ($\lambda_{real}$) can then be compared to the calculated thermal conductivity ($\lambda_{surrogate}$) of the approximated gas mixture, which is composed of $X_{CH4}$, $Y_{Inert}$, and $Y_{surrogate}$. If the absolute value of the percentage difference between the calculated and measured thermal conductivities is less than a threshold (e.g., 10%) 222, then the selected surrogate is not revised (e.g., $Y_{surrogate}$ remains selected as a combination of ethane ($Y_{C2H6}$) and propane ($Y_{C3H8}$)). However, if the absolute value of percentage difference 222 is greater than or equal to 10%, then additional analysis may be performed to determine how to revise the selected surrogate. For example, if the percentage difference 224 is less than or equal to negative 10%, then the surrogate may be revised 226 and selected to be propane ($Y_{C3H8}$). If the percentage difference 228 is greater than or equal to 10%, then the surrogate may be revised and selected as a combination 230 of propane ($Y_{C3H8}$) and pentane ($Y_{C5H12}$). In one embodiment, the combination includes 20% propane and 80% pentane. It should be understood that the scope of the present disclosure is not limited to a threshold of 10% and a 20%-80% combination of propane and pentane, and other thresholds and combinations may be used.

After a surrogate ($Y_{surrogate}$) is selected for the LHV determination of process 200, the LHV may be calculated 232 based on the approximated gas mixture composition, which consists of the methane concentration ($X_{CH4}$), the selected surrogate ($Y_{surrogate}$), and the inert concentration ($Y_{Inert}$). The LHV may be determined according to International Organization for Standardization (ISO) standards (e.g., ISO 6976) related to calculating a lower heating value. As a result 234, the calculated estimate of the LHV, the methane concentration ($X_{CH4}$), the non-methane hydrocarbon concentration ($X_{NMHC}$), and any other values determined herein, may be fed forward to the control systems of an engine.

Figure 3:
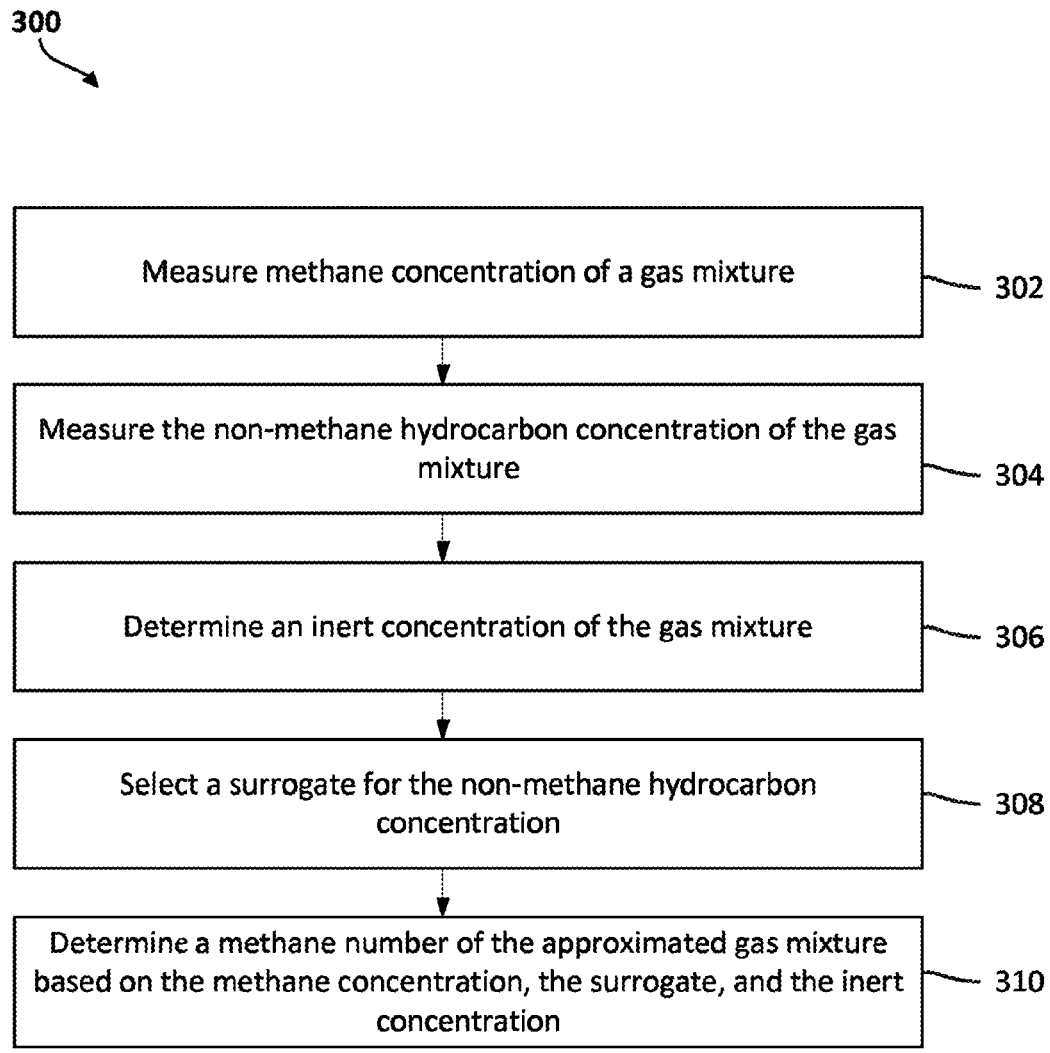
FIG. 3 is a flowchart of a process for determining the combustion properties of a wellhead gas, according to an exemplary embodiment.

Referring to FIG. 3, a flow diagram of a process 300 for determining combustion properties of wellhead gas, is shown, according to an exemplary embodiment. In alternative embodiments, fewer, additional, and/or different steps may be performed. Also, the use of a flow diagram is not meant to be limiting with respect to the order of steps performed. Process 300 includes measuring the methane concentration of a gas mixture (302) and measuring the non-methane hydrocarbon concentration of the gas mixture (304). One or more methane sensors may be used to take such measurements. In one embodiment, a laser-based $CH_4$ sensor is used. The inert content concentration of the gas mixture is then determined (306). In one embodiment, the inert concentration is calculated as $Y_{Inert}=1-X_{CH4}-X_{NMHC}$. A surrogate is selected for the non-methane hydrocarbon concentration (308). For example, the surrogate may be selected from one or more potential surrogates based on comparison of the non-methane hydrocarbon concentration to a threshold. The methane number of the approximated gas mixture is then determined based on the methane concentration, the selected surrogate, and the inert concentration (310). In an embodiment, the methane number is determined according to ISO standards with respect to methane number calculations.

Figure 4:
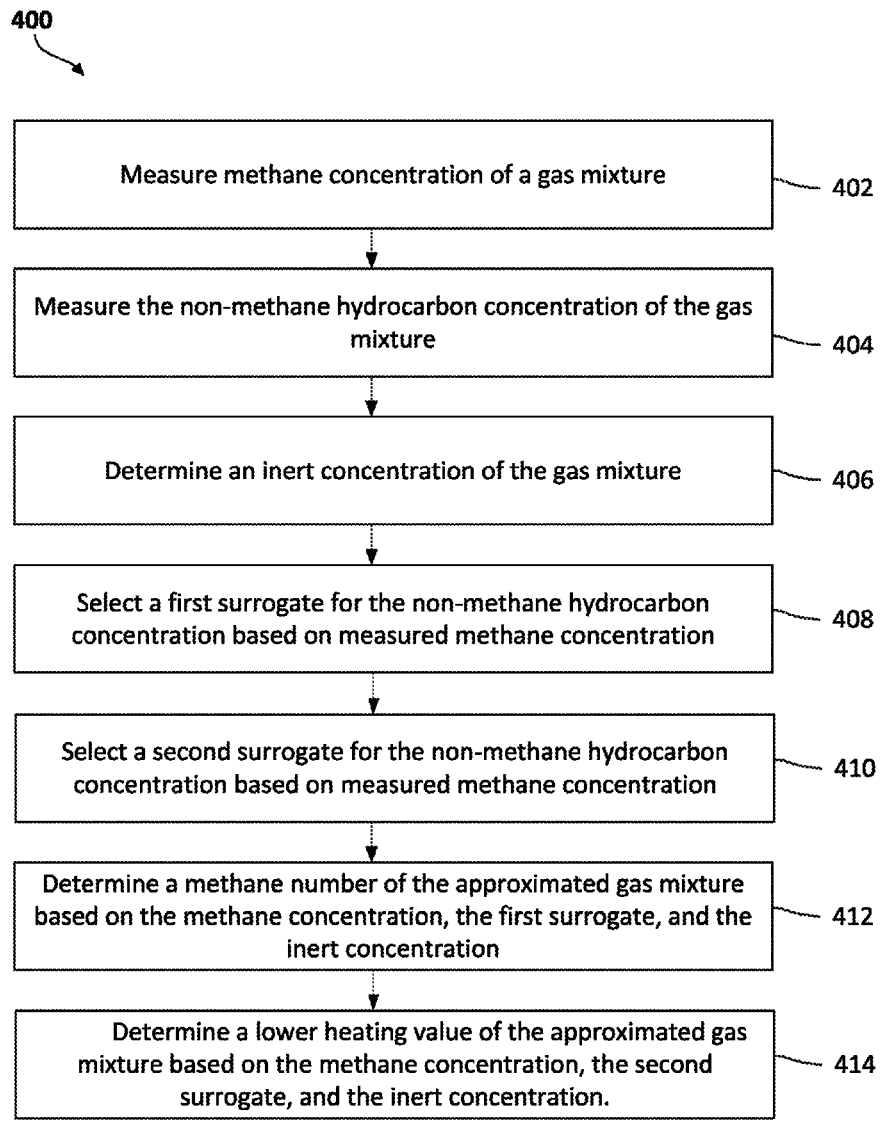
FIG. 4 is a flowchart of a process for determining the combustion properties of a wellhead gas, according to another exemplary embodiment.

Referring to FIG. 4, a flow diagram of a process 400 for determining combustion properties of wellhead gas, is shown, according to another exemplary embodiment. In alternative embodiments, fewer, additional, and/or different steps may be performed. Also, the use of a flow diagram is not meant to be limiting with respect to the order of steps performed. Process 400 includes measuring the methane concentration of a gas mixture (402), measuring the non-methane hydrocarbon concentration of the gas mixture (404), and determining the inert content concentration of the gas mixture (406). A first surrogate is selected for the non-methane hydrocarbon concentration (408), and a second surrogate is selected for the non-methane hydrocarbon concentration (410). For example, the first and second surrogates may each be selected from one or more potential surrogates based on comparison of the non-methane hydrocarbon concentration to a threshold. The methane number of the approximated gas mixture is determined based on the methane concentration, the selected first surrogate, and the inert concentration (412). The lower heating value of the approximated gas mixture is determined based on the methane concentration, the selected second surrogate, and the inert concentration (414). In an embodiment, the methane number and lower heating value are calculated according to ISO standards with respect to methane number and lower heating value calculations. After estimating the methane number and lower heating value using the surrogates in this manner, the methane number and lower heating may each be used (fed forward) to a combustion engine's control systems.

Figure 5:
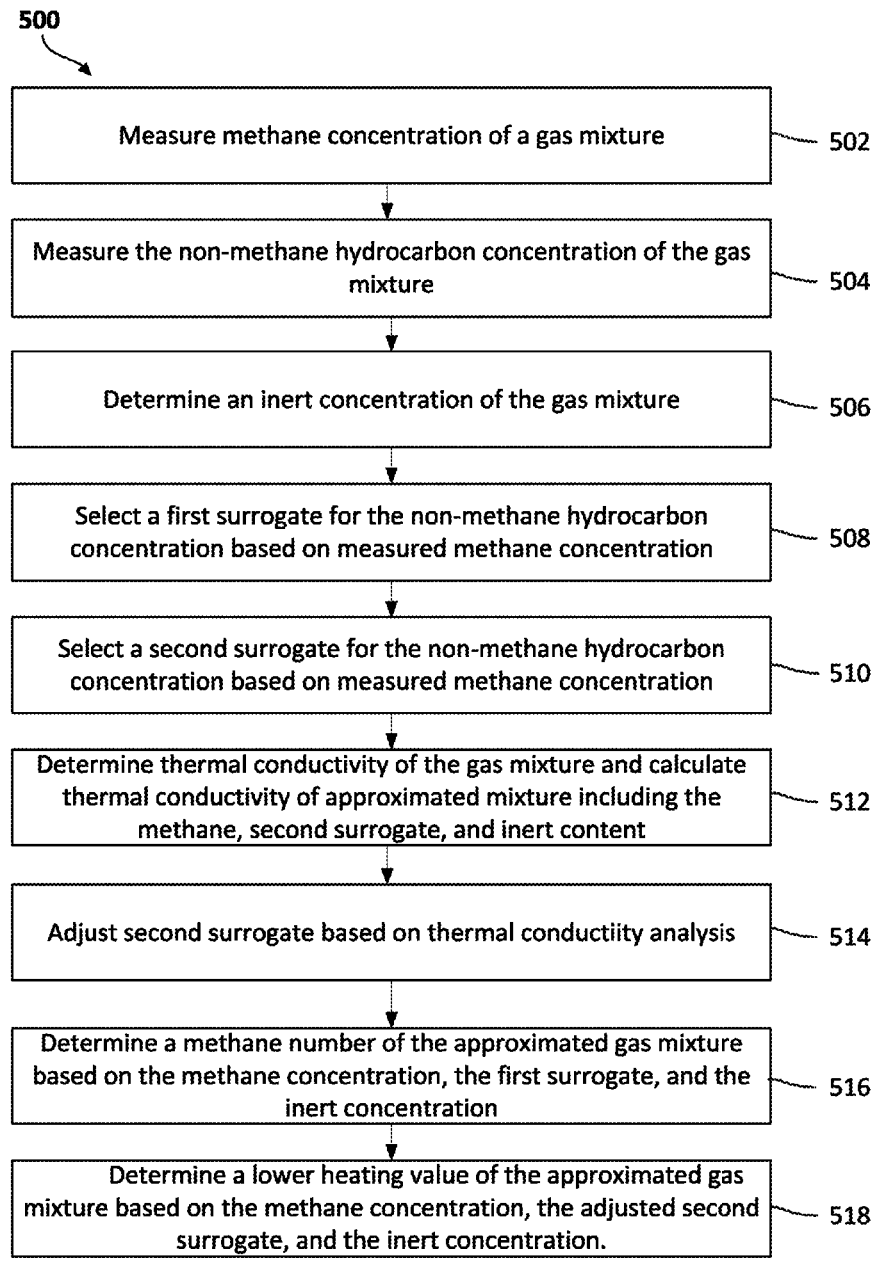
FIG. 5 is a flowchart of a process for determining the combustion properties of a wellhead gas, according to another exemplary embodiment.

Referring to FIG. 5, a flow diagram of a process 500 for determining combustion properties of wellhead gas, is shown, according to another exemplary embodiment. In alternative embodiments, fewer, additional, and/or different steps may be performed. Also, the use of a flow diagram is not meant to be limiting with respect to the order of steps performed. Process 500 includes measuring the methane concentration of a gas mixture (502), measuring the non-methane hydrocarbon concentration of the gas mixture (504), and determining the inert content concentration of the gas mixture (506). A first surrogate is selected for the non-methane hydrocarbon concentration (508), and a second surrogate is selected for the non-methane hydrocarbon concentration (510). The first and second surrogates may each be selected from one or more potential surrogates based on comparison of the non-methane hydrocarbon concentration to a threshold. The thermal conductivity of the actual gas mixture is determined, and the thermal conductivity of the approximated mixture comprised of methane, the selected second surrogate, and inert content is calculated (512). A thermal conductivity detector may be used to determine actual thermal conductivity values of the gas mixture. Based on a comparison of the thermal conductivity of the actual gas mixture to the calculated thermal conductivity of the approximated mixture (containing the second surrogate), the second surrogate may be adjusted to a different second surrogate (514). For example, the percentage difference between the actual and calculated thermal conductivities may be compared to a threshold, and the second surrogate may be revised based on how the percentage difference compares to the threshold. The methane number of the approximated gas mixture is determined based on the methane concentration, the selected first surrogate, and the inert concentration (516). The lower heating value of the approximated gas mixture is determined based on the methane concentration, the adjusted second surrogate, and the inert concentration (518). In an embodiment, the methane number and lower heating value are calculated according to ISO standards with respect to methane number and lower heating value calculations.

Figure 6:
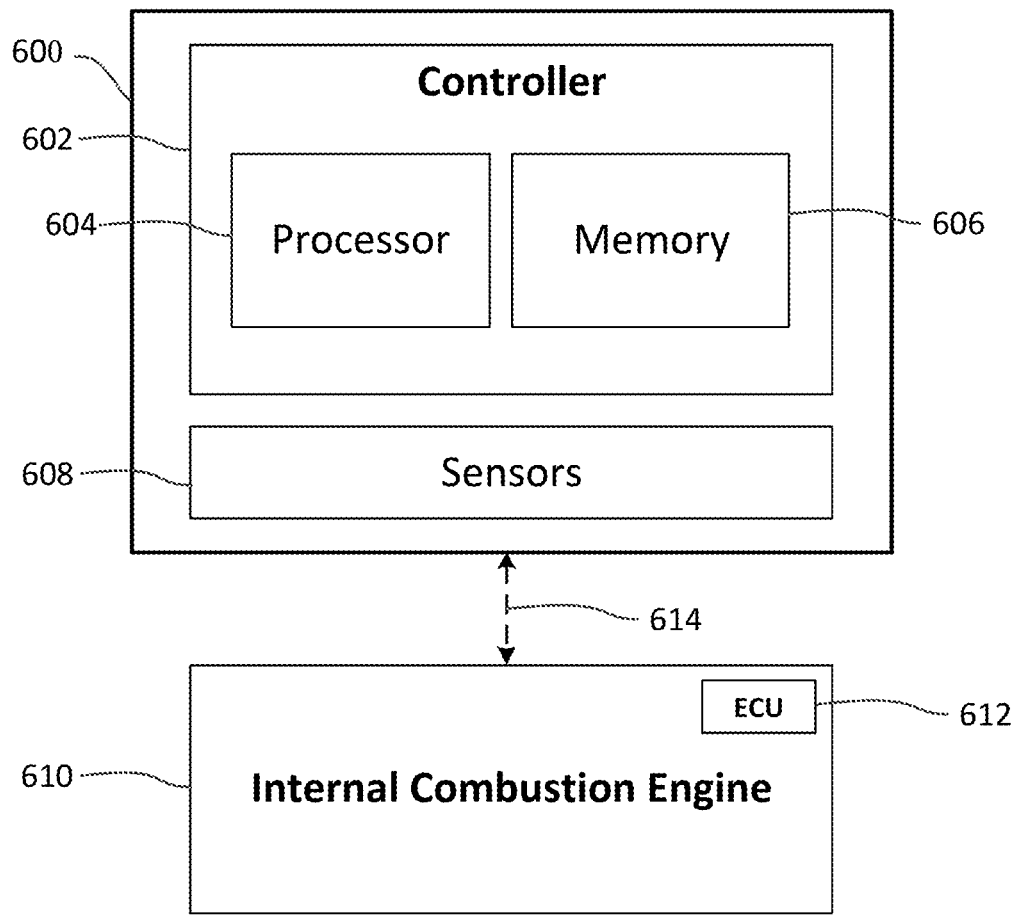
FIG. 6 shows a system for implementing the techniques and methods described herein for determining combustion properties of wellhead gas, according to an exemplary embodiment.

FIG. 6 shows system 600 that may be used to implement the techniques and methods described herein for determining combustion properties of wellhead gas, according to an exemplary embodiment. System 600 typically includes a controller 602 having at least one processor 604 coupled to a memory 606. Processor 604 may be any commercially available CPU. Processor 604 may represent one or more processors and may be implemented as a general-purpose processor, an application specific integrated circuit (ASIC), one or more field programmable gate arrays (FPGAs), a digital-signal-processor (DSP), a group of processing components, or other suitable electronic processing components. Memory 606 may include random access memory (RAM) devices comprising a main storage of the controller 602, as well as any supplemental levels of memory, e.g., cache memories, non-volatile or back-up memories (e.g., programmable or flash memories), read-only memories, etc. In addition, memory 606 may include memory storage physically located elsewhere in system 600 or controller 602, e.g., any cache memory in the processor 604 as well as any storage capacity used as a virtual memory, e.g., as stored on a mass storage device, etc.

In certain embodiments, controller 602 forms a portion of a processing subsystem including one or more computing devices having memory, processing, and communication hardware. Controller 602 may be a single device or a distributed device, and the functions of controller 602 may be performed by hardware and/or as computer instructions on a non-transient computer readable storage medium, and functions may be distributed across various hardware or computer based components. In certain embodiments, controller 602 is part of the control system of a combustion engine (e.g., controller 602 may be part of or form an engine control unit (ECU) 612 of internal combustion engine 610). In other embodiments, controller 602 is separate from internal combustion engine 610. For example, system 600 may be integrated into a wellhead (or along a distribution pipe of a wellhead) such that the composition of the gas mixture drawn from the wellhead and supplied to internal combustion engine 610 may be approximated according to the techniques disclosed herein.

In one embodiment, the gas mixture drawn from the wellhead is approximated by controller 602, and properties of the gas mixture determined by controller 602 are fed forward to internal combustion engine 610. Data determined by controller 602 can be transmitted via communication pathway 614, which connects controller 602 and ECU 612 of internal combustion engine 610. Communication pathway 614 may include any commercially available communication networks (wired and/or wireless). The determined properties of the gas mixture (e.g., the methane number (MN) of the gas mixture, the lower heating value (LHV) of the gas mixture, etc.) can be used by ECU 612 of internal combustion engine 610 to adjust various operational characteristics of internal combustion engine 610. For example, ECU 612 can interpret the data provided by controller 602 in order to control various actuators of internal combustion engine 610 to ensure optimal engine performance based on the arriving wellhead gas mixture. ECU 612 may use the data to adjust engine characteristics such as air/fuel mixture, ignition timing, valve timing, idle speeds, fueling rates, among others. ECU 612 may include at least one processor, memory, and other circuitry required to control an internal combustion engine. ECU 612 may be any commercially available ECU unit.

In general, the routines executed to implement the embodiments may be implemented as part of an operating system or a specific application, module, or sequence of instructions. In certain embodiments, controller 602 includes one or more modules structured to functionally execute the operations of controller 602 to determine combustion properties of wellhead gas. The description herein including modules emphasizes the structural independence of the aspects of the controller 602, and illustrates one grouping of operations and responsibilities of the controller 602. More specific descriptions of certain embodiments of controller 602 operations are described by the sections herein referencing FIGS. 1-5. Other groupings that execute similar overall operations are understood within the scope of the present application. The modules typically comprise one or more instructions set at various times in various memory and storage devices in a computer, and that, when read and executed by one or more processors in a computer, cause the computer to perform operations necessary to execute elements of disclosed embodiments. Moreover, various embodiments have been described in the context of fully functioning computers and computer systems, those skilled in the art will appreciate that the various embodiments are capable of being distributed as a program product in a variety of forms, and that this applies equally regardless of the particular type of computer-readable media used to actually effect the distribution. Examples of computer-readable media include but are not limited to recordable type media such as volatile and non-volatile memory devices, floppy and other removable disks, hard disk drives, optical disks, flash memory, among others.

Example and non-limiting module implementation elements include sensors 608 (e.g., a laser-based $CH_4$ sensor, a thermal conductivity detector, etc.), which are communicably coupled to controller 602 and provide any value determined herein. Example and non-limiting module implementation elements may further include sensors 608 providing any value that is a precursor to a value determined herein, datalinks and/or network hardware including communication chips, oscillating crystals, communication links, cables, twisted pair wiring, coaxial wiring, shielded wiring, transmitters, receivers, and/or transceivers, logic circuits, hardwired logic circuits, reconfigurable logic circuits in a particular non-transient state configured according to the module specification, any actuator including at least an electrical, hydraulic, or pneumatic actuator, a solenoid, an op-amp, analog control elements (springs, filters, integrators, adders, dividers, gain elements), and/or digital control elements.

In the above description numerous specific details are set forth for purposes of explanation. It will be apparent, however, to one skilled in the art that these specific details are merely examples. In other instances, structures and devices are shown only in block diagram form in order to avoid obscuring the teachings.

Reference in this specification to "one embodiment," "an embodiment," or "an exemplary embodiment" means that a particular feature, structure, or characteristic described in connection with the embodiment is included in at least one embodiment. The appearance of the phrase "in one embodiment" in various places in the specification is not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

While certain exemplary embodiments have been described and shown in the accompanying drawings, it is to be understood that such embodiments are merely illustrative and not restrictive of the disclosed embodiments and that these embodiments are not limited to the specific constructions and arrangements shown and described, since various other modifications may occur to those ordinarily skilled in the art upon studying this disclosure. In an area of technology such as this, where growth is fast and further advancements are not easily foreseen, the disclosed embodiments may be readily modifiable in arrangement and detail as facilitated by enabling technological advancements without departing from the principals of the present disclosure.

What is claimed is:

1. A method comprising:
   measuring a methane concentration of a gas mixture;
   measuring a non-methane hydrocarbon concentration of the gas mixture;
   calculating an inert concentration of the gas mixture;
   selecting a first surrogate for the non-methane hydrocarbon concentration; and
   determining, using a computing device, a methane number of the gas mixture, wherein the methane number is based on the methane concentration, the first surrogate, and the inert concentration;
   wherein the first surrogate is selected as propane if the methane concentration is greater than a first threshold, and wherein the first surrogate is selected as pentane if the methane concentration is less than or equal to the first threshold.

2. The method of claim 1, wherein the first threshold is 50 percent.

3. The method of claim 1, further comprising:
   selecting a second surrogate for the non-methane hydrocarbon concentration; and
   determining, using the computing device, a lower heating value of the gas mixture, wherein the lower heating value is based on the methane concentration, the second surrogate, and the inert concentration.

4. The method of claim 3, wherein the second surrogate is selected as a combination of ethane and propane when the methane concentration is greater than a second threshold, and wherein the second surrogate is selected as pentane when the methane concentration is less than or equal to the second threshold.

5. The method of claim 4, wherein the second threshold is 20 percent.

6. The method of claim 4, wherein the combination of ethane and propane comprises 30 percent ethane and 70 percent propane.

7. The method of claim 1, wherein the gas mixture comprises internal combustion engine gas.

8. A system comprising:
   one or more computing devices configured to:
   measure a methane concentration of a gas mixture;
   measure a non-methane hydrocarbon concentration of the gas mixture;
   calculate an inert concentration of the gas mixture;
   select a first surrogate for the non-methane hydrocarbon concentration; and
   determine a methane number of the gas mixture, wherein the methane number is based on the methane concentration, the first surrogate, and the inert concentration;
   wherein the first surrogate is selected as propane if the methane concentration is greater than a first threshold, and wherein the first surrogate is selected as pentane if the methane concentration is less than or equal to the first threshold.

9. The system of claim 8, wherein the one or more computing devices are further configured to:
   select a second surrogate for the non-methane hydrocarbon concentration; and
   determine a lower heating value of the gas mixture, wherein the lower heating value is based on the methane concentration, the second surrogate, and the inert concentration.

10. The system of claim 9, wherein the second surrogate is selected as a combination of ethane and propane when the methane concentration is greater than a second threshold, and wherein the second surrogate is selected as pentane when the methane concentration is less than or equal to the second threshold.

11. The system of claim 10, wherein the combination of ethane and propane comprises 30 percent ethane and 70 percent propane.

12. A method comprising:
measuring a methane concentration of a gas mixture;
measuring a non-methane hydrocarbon concentration of the gas mixture;
calculating an inert concentration of the gas mixture;
selecting a first surrogate for the non-methane hydrocarbon concentration, wherein the first surrogate is selected as propane if the methane concentration is greater than a first threshold, and wherein the first surrogate is selected as pentane if the methane concentration is less than or equal to the first threshold; and
determining, using a computing device, a methane number of the gas mixture, wherein the methane number is based on the methane concentration, the first surrogate, and the inert concentration;
selecting a second surrogate for the non-methane hydrocarbon concentration, wherein the second surrogate is selected as a combination of ethane and propane when the methane concentration is greater than a second threshold, and wherein the second surrogate is selected as pentane when the methane concentration is less than or equal to the second threshold;
determining a thermal conductivity of an approximated mixture comprising the methane concentration, the second surrogate, and the inert concentration;
determining a difference between the approximated mixture thermal conductivity and a thermal conductivity of the gas mixture;
adjusting the second surrogate based on a third threshold and the difference between the approximated mixture thermal conductivity and the gas mixture thermal conductivity; and
determining, using the computing device, a lower heating value of the gas mixture, wherein the lower heating value is based on the methane concentration, the second surrogate, and the inert concentration.

13. The method of claim 12, wherein adjusting the second surrogate based on the third threshold and the difference comprises adjusting the second surrogate to be propane.

14. The method of claim 12, wherein adjusting the second surrogate based on the third threshold and the difference comprises adjusting the second surrogate to be a combination of pentane and hexane.

15. The method of claim 13, wherein the combination of pentane and hexane comprises 50 percent pentane and 50 percent hexane.

16. The method of claim 12, wherein adjusting the second surrogate based on the third threshold and the difference comprises adjusting the second surrogate to be a combination of propane and pentane.

17. The method of claim 16, wherein the combination of propane and pentane comprises 20 percent propane and 80 percent pentane.

18. The method of claim 12, wherein the third threshold is 10 percent.

* * * * *